United States Patent [19]

Nomura

[11] Patent Number: 4,936,993

[45] Date of Patent: Jun. 26, 1990

[54] APPARATUS FOR SEPARATION OF BLOOD COMPONENTS

[75] Inventor: Kazuhide Nomura, Fujinomiya, Japan

[73] Assignee: Terumo Kabushiki Kaisha, Tokyo, Japan

[21] Appl. No.: 294,696

[22] PCT Filed: Jun. 29, 1987

[86] PCT No.: PCT/JP87/00438

§ 371 Date: Dec. 21, 1988

§ 102(e) Date: Dec. 21, 1988

[87] PCT Pub. No.: WO88/00063

PCT Pub. Date: Jan. 14, 1988

[30] Foreign Application Priority Data

Jul. 1, 1986 [JP] Japan ............................ 61-152687

[51] Int. Cl.$^5$ ............................................. B01D 24/12
[52] U.S. Cl. ................................. 210/446; 210/435; 210/491; 210/492; 210/505
[58] Field of Search ............... 210/491, 492, 508, 505, 210/502.1, 435, 446, 489

[56] References Cited

U.S. PATENT DOCUMENTS

| | | | |
|---|---|---|---|
| 4,130,642 | 12/1978 | Kikugawa | 424/101 |
| 4,246,107 | 1/1981 | Takenaka | 210/806 |
| 4,330,410 | 5/1982 | Takenaka | 210/767 |
| 4,596,657 | 6/1986 | Wisdom | 210/257.1 |
| 4,701,267 | 10/1987 | Watanabe et al. | 210/491 |
| 4,810,378 | 3/1989 | Carmen et al. | 210/508 |
| 4,810,394 | 3/1989 | Masuda | 210/491 |

FOREIGN PATENT DOCUMENTS

| | | |
|---|---|---|
| 55-23805 | 6/1980 | Japan . |
| 55-135750 | 10/1980 | Japan . |
| 58-54125 | 12/1983 | Japan . |
| 58-54132 | 12/1983 | Japan . |

*Primary Examiner*—W. Gary Jones
*Attorney, Agent, or Firm*—Frishauf, Holtz, Goodman & Woodward

[57] ABSTRACT

An apparatus for the separation of blood components, specifically for the removal of white blood cells and blood platelets from blood comprises a tubular housing providing at one end thereof with a blood inlet and at the other end thereof with a blood outlet and an aggregate layer of fibers capable of sequestering white blood cells and blood platelets packed in the housing. The aggregate layer of fibers comprises a blood inlet side layer of a bulk density of not less than 0.16 g/cm$^3$ and less than 0.21 g/cm$^3$ and a blood outlet side layer of a bulk density of not less than 0.21 g/cm$^3$ and not more than 0.23 g/cm$^3$ and is packed in a ratio in the range of 0.04 to 0.09 g per ml of the flow volume of blood under treatment.

3 Claims, 1 Drawing Sheet

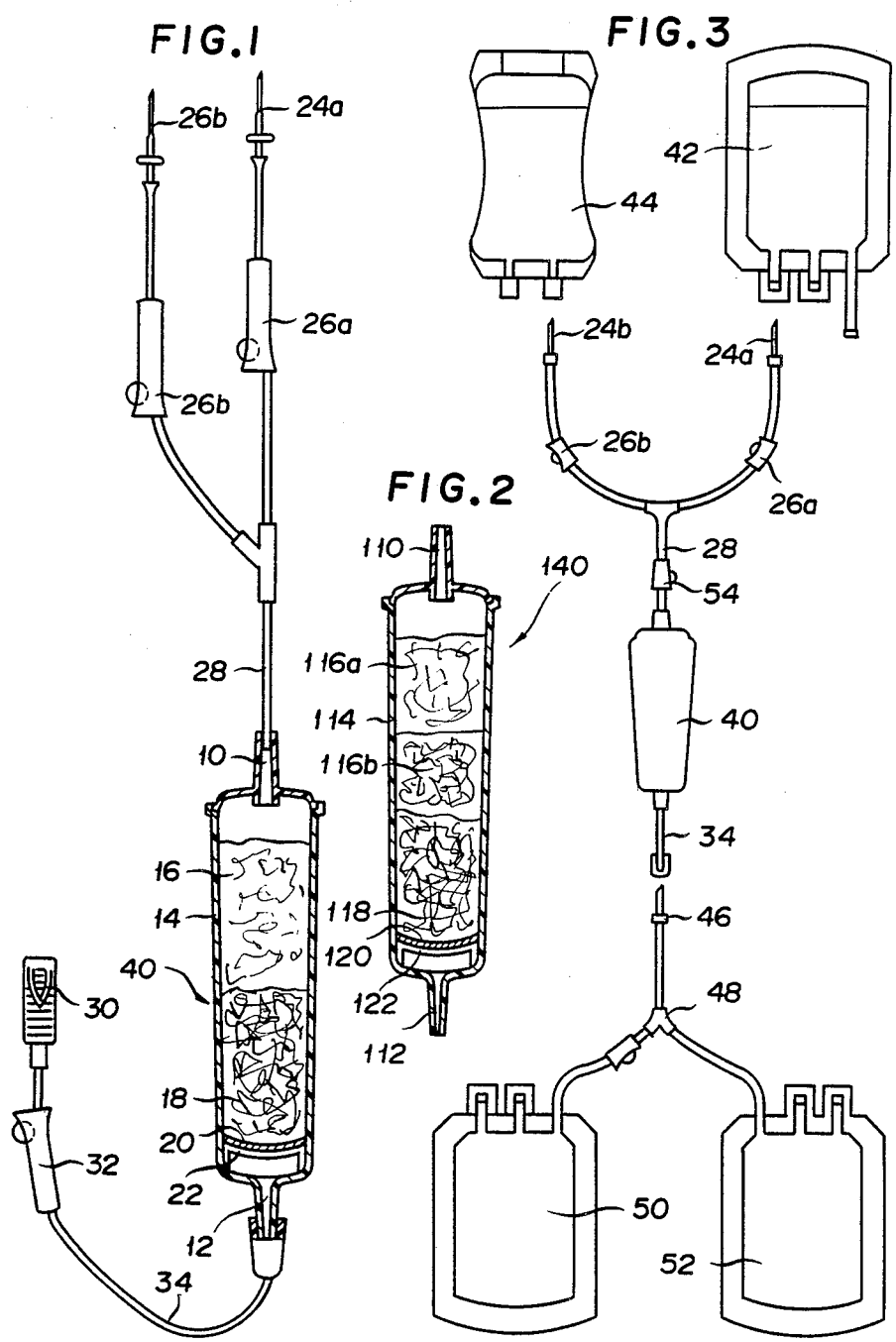

APPARATUS FOR SEPARATION OF BLOOD COMPONENTS

TECHNICAL FIELD

This invention relates to an apparatus for the separation of blood components. More particularly, it relates to an apparatus for the separation of blood components, specifically for the removal of white blood cells and blood platelets from blood.

BACKGROUND ART

Heretofore in the therapy by blood transfusion, more often than not whole-blood preparations of red blood cell preparations have been used. These preparations, however, inevitably contain the white blood cell antibody and the blood platelet antibody and pose as a problem the possibility of the antibodies giving rise to secondary reactions. As a solution to this problem, the practice of removing of white blood cells and blood platelets from the whole-blood preparations and the red blood cell preparations has been heretofore in vogue. As means for the separation of blood components, specifically for the removal of white blood cells and blood platelets from the whole blood or from the red blood component, there has been proposed an apparatus which is obtained by filling a housing with defatted and bleached Egyptian cotton in uniform density (Japanese Patent Publication NO. SHO 55(1980)-23,805).

When an apparatus of this nature is used, however, the degree with which the removal of white blood cells and blood platelets is attained hinges on he density of packing of the Egyptian cotton and the efficiency of this removal is improved but the speed of passage of blood through aggregate of cotton is lowered and the time required for the treatment is lengthened in proportion as the density of packing is increased. Conversely, the speed of passage of blood is heightened but the efficiency of removal is lowered in proportion as the density of packing is lowered. Thus, the apparatus is hardly practicable.

An object of this invention, therefore, is to provide a novel apparatus for the removal of blood components.

Another object of this invention is to provide an apparatus for the separation of blood components, which permits quick passage of blood under treatment and warrants a reduction in the time for the treatment at no sacrifice of the efficiency of removal of white blood cells and blood platelets.

DISCLOSURE OF THE INVENTION

The objects described above are accomplished by an apparatus for the separation of blood components, which comprises a tubular housing provided at one end thereof with a blood inlet and at the other end thereof with a blood outlet and a layer of aggregate of fibers capable of sequestering white blood cells and blood platelets packed in the housing, the layer of aggregate of fibers comprising of a blood inlet side layer having a bulk density of not less than 0.16 g/cm$^3$ and less than 0.21 g /cm$^3$ and a blood outlet side layer having a bulk density of not less than 0.21 g/cm$^3$ and not more than 0.23 g/cm$^3$ and being packed at a density in the range of 0.04 to 0.09 g per ml of the flow volume of blood under treatment.

This invention also concerns an apparatus for the separation of blood components, wherein the fibers packed in the form of a layer of aggregate are single fibers. This invention further concerns an apparatus for the removal of blood components, wherein the fibers are natural fibers such as of cotton or synthetic fibers such as of polyester, polyacrlylonitrile, polyamide, or cellulose acetate. This invention concerns an apparatus for the separation of blood components, wherein the fibers are defatted and bleached fibers of Egyptian cotton. This invention also concerns an apparatus for the separation of blood components, wherein the blood inlet side layer comprises a first layer having a blood inlet side bulk density of not less than 0.16 g/cm$^3$ and less than 0.19 g/cm$^3$ and a second layer having a blood outlet side bulk density of not less than 0.19 g/cm$^3$ and less than 0.21 g/cm$^3$.

BRIEF DESCRIPTION OF DRAWINGS

FIG. 1 is a partially sectioned side view of a typical apparatus for the separation of blood components as one embodiment of the present invention, FIG. 2 is a cross section of a typical apparatus as another embodiment of the invention, and FIG. 3 is an artist's concept of a typical method for the use of the apparatus for the separation of blood components illustrated in FIG. 1.

BEST MODE FOR CARRYING OUT THE INVENTION

Now, the present invention will be described in detail below with reference to the accompanying drawings An apparatus 40 for the separation of blood components illustrated as one embodiment of the present invention in FIG. 1 has fiber aggregate layers 16 and 18 differing mutually in bulk density packed in a tubular housing 14 which is provided at one end thereof with a blood inlet 10 and at the other end thereof with a blood outlet 12. The fiber aggregate layers 16 and 18 are formed of fibers capable of sequestering white blood cells and blood platelets. The layer 16 which falls on the blood inlet side possesses a bulk density of not less than 0.16 g/cm$^3$ and less than 0.21 g/cm$^3$, preferably not less than 0.17 g/cm$^3$ and less than 0.19 g/cm$^3$, and the layer 18 which falls on the blood outlet side possesses a bulk density of not less than 0.21 g/cm$^3$ and not more than 0.23 g/cm$^3$, preferably not less than 0.21 g/cm$^3$ and not more than 0.22 g/cm$^3$. The ratio by weight of the blood inlet side layer 16 to the blood outlet side layer 18 so packed in the housing is in the range of 80:70 to 50:50, preferably 75:25 to 60:40.

The housing 14 is provided near the blood inlet 10 and the blood outlet 12 each with a filter 20 which is adapted to prevent the fiber aggregate from loss due to disintegration or entrainment. To the blood inlet 10 is connected a tube 28 which is generally provided at the leading ends of the branching legs thereof with hollow needless 24a, 24b and optionally provided halfway along the lengths of the branching legs thereof with clamps 26a, 26b. To the blood outlet 12 is connected a tube 34 which is provided at the leading end thereof with a liquid mixing port 30 and optionally provided halfway along the length thereof with a clamp 32.

FIG. 2 illustrates another embodiment of this invention. In an apparatus 140 similar to the apparatus of the embodiment of FIG. 1, a layer corresponding to the blood inlet side layer 16 comprises a first layer 116a and a second layer 116b differing mutually in bulk density. Specifically, inside a tubular housing 124 provided at the upper end thereof with a blood inlet 120 and at the lower end thereof with a blood outlet 122, there are disposed a first blood inlet side layer 116a of a bulk density of not less than 0.16 g/cm$^3$ and less than 0.19 g/cm$^3$, preferably not less than 0.17 g/cm$^3$ and less than 0.18 g/cm$^3$, a second blood inlet side layer 116b of a bulk density of not less than 0.19 g/cm$^3$ and less than 0.21 g/cm$^3$, preferably not less than 0.19 g/cm$^3$ and less than 0.20 g/cm$^3$, and a blood outlet side layer 118 of a bulk density of not less than 0.21 g/cm$^3$ and not more than 0.23 g/cm$^3$, preferably not less than 0.21 g/cm$^3$ and not more than 0.22 g/cm$^3$, as increasingly separated from the blood inlet 120 side of the housing 124. The ratio by weight of the blood inlet side layer (the sum of the first layer 116a and the second layer 116b) to the blood outlet side layer 118 packed in the housing is in the range of 80:20 to 50:50, preferably 75:25 to 60:40, and the ratio by weight of the first layer 116a to the second layer 116b is in the range of 70:30 to 30:70, preferably 60:40 to 40:60. The reference numerals of FIG. 2 which are the sums of those of FIG. 1 respectively plus 100 denote the same parts as those of FIG. 1.

If the bulk density of the blood inlet side layer 16 or 116a and 116b and the bulk density of the blood outlet side layer 18 or 118 are larger than the respective upper limits of the aforementioned ranges, the speed of flow of blood is unduly low. If they are smaller than the respective lower limits, the ratios of removal of white blood cells and blood platelets are unduly low. The ratio of packing of the fiber aggregate is in the range of 0.04 to 0.09 g, preferably 0.05 to 0.07 g per ml of the flow volume of blood under treatment. If the ratio of packing is less than 0.04 g, the efficiency of removal of white blood cells and blood platelets is unduly low. If it exceeds 0.09 g, the resistance to the flow of blood is too large to obtain a satisfactory speed of flow.

To be suitably used for the present invention, the fibers selected are only required to be capable of sequestering white blood cells and blood platelets. As examples of fibers satisfying the requirement, natural cottons such as Egyptian cotton, American cotton, and Asian cotton and synthetic fibers such as of polyester, polyacrylonitrile, polyamide, and cellulose acetate can be cited. These fibers are used in the form of staple fibers having diameters in the range of 10 to 25 microns, preferably 13 to 18 microns and lengths in the range of 20 to 40 mm, preferably 30 to 40 mm. Among other species of fibers enumerated above, defatted and bleached fibers of Egyptian cotton prove to be particularly desirable.

Natural cottons are broadly classified under three kinds by districts of production, i.e. Egyptian cotton (*Gossypium barbadense*), American cotton or Upland cotton (*G. hirsutum*), and Asian cotton or Indian cotton (*G. atrboreum* or *G. herbaceum*). The average fiber length, average diameter, and twists of these cottons are as follows.

| Kind | Average fiber length (mm) | Average diameter (microns) | Twist (/cm) |
|---|---|---|---|
| Egyptian cotton | 35.6 | 16.3 | 70–112 |
| Upland cotton | 25.4 | 20 | 56–96 |
| Asian cotton | 20 | 21 | 48–76 |

In these cottons, the Egyptian cotton which is a natural cotton having the largest average fiber length and the smallest average diameter shows the highest ratio of removal of white blood cells and blood platelets. Preferably, the natural cotton is used in a defatted and bleached form. The defatting and bleaching of fibers is carried out by following with necessary modifications the method for production of absorbent cotton specified in the Japanese pharmacopoeia, i.e. by treating the fibers with the combination of sodium hydroxide and hypochlorous acid or the combination of sodium hydroxide and hydrogen peroxide. By this treatment, the Egyptian cotton or other natural cotton is deprived of impurities and is thence prevented from releasing colored substances and impurities through oxidation.

The housing is not specifically required to have cylindrical shape but allowed to have the shape of a column of a desired section. The material for this housing may be polyethylene, polypropylene, vinyl chloride resin, polystyrene, ABS resin, or polycarbonate. Among other materials cited above, the ABS resin proves to be particularly desirable.

The specific forms of blood which the apparatus of this invention is principally intended to separate are fresh blood incorporating therein a suitable anticoagulant and a concentrated solution of red blood cells. This invention, however, is not limited thereto. Any liquid containing floating blood cells can be subjected to separation by the apparatus of this invention. As the anticoagulant to be added to fresh blood, there can be used heparin, ACD (acid-citrate-dextrose) liquid, or CPD (citrate-phosphate-dextrose) liquid. When the concentrated solution of red blood cells is to be separated, it has the hematocrit value thereof adjusted in the range of 40 to 60 by the addition of physiological saline solution before it is put to use. The operation of separation of the blood by the use of apparatus of this invention is carried out at a temperature in the range of 0° to 38° C. Practical use of the apparatus 40 (or 140) of the present invention for the separation of blood components is effected by connecting the hollow needle 24a to a container 42 holding either whole blood or a concentrated solution of red blood cells (blood bag) and the hollow needle 24b to a container 44 holding the physiological saline solution, connecting the blood outlet 12 to a hollow needle 46 for further communication via a forked tube 48 with blood bags made of vinyl chloride resin or empty containers 50, 52 made of glass, closing the clamp 26a, and then opening the clamp 26b thereby allowing the physiological saline solution held in the container 44 to flow into the apparatus 40 for separation of blood components, wash the fiber aggregate layers 16, 18, and depart from the blood outlet and flow into the empty container 52. Actual use of the apparatus for separation of the concentrated solution of red blood cells is effected by opening the clamps 26a, 26b and closing the clamp 54 thereby advancing the flow of the phsyiological saline solution to the blood bag 42 and adjusting the hematocrit value of the red blood cells in the range of 40 to 60, then closing the clamp 26b and opening the clamp 54 thereby allowing the blood to flow into the apparatus 40, depart from the blood outlet, and enter another empty container 50, and closing the clamp 26a and opening the clamp 26b thereby allowing a suitable amount of the physiological saline solution to flow through and wash the fiber aggregate layers 16, 18, and finally enter the empty container 50. For the separation of whole blood, it is not always necessary to use the physiological saline solution for adjusting the hematocrit value. The apparatus 140 illustrated in FIG. 2 is used in the same way as the apparatus 40 of FIG. 1.

During the operation described above, when the blood flowing in through the blood inlet 10 is passing through the blood inlet side layer 16, of the fiber aggregate layers 16, 18, chiefly white blood cells and blood platelets which have relatively large particle diameters corresponding to the size of interstices proper to the bulk density of the layer 16 are first sequestered. The portions of white blood cells and blood platelets which have escaped the sequestration are captured in the blood outlet side layer 18. Thus, the fiber aggregate layers 16, 18 suffer from far less clogging and permit much quicker flow of blood than a fiber aggregate layer which is packed in a uniform bulk density.

The expression "sequestration of white blood cells and blood platelets" as used in the present invention means accumulation of white blood cells and blood platelets in the aggregates of fibers packed in the apparatus.

Now, the present invention will be described more specifically below with reference to working examples. The terms "ratio of removal" and "ratio of recovery" used in the following working examples are defined as follows.

$$\text{Ratio of removal (\%)} = \frac{\left(\begin{array}{c}\text{Number of white}\\\text{blood cells}\\\text{before filtration}\end{array}\right) - \left(\begin{array}{c}\text{Number of white}\\\text{blood cells}\\\text{after filtration}\end{array}\right)}{\text{Number of white blood cells before filtration}} \times 100$$

$$\text{Ratio of removal (\%)} = \frac{\left(\begin{array}{c}\text{Number of}\\\text{blood platelets}\\\text{before filtration}\end{array}\right) - \left(\begin{array}{c}\text{Number of}\\\text{blood plates}\\\text{after filtration}\end{array}\right)}{\text{Number of blood platelets before filtration}} \times 100$$

$$\text{Ratio of recovery (\%)} = \frac{\text{Number of red blood cells after filtration}}{\text{Number of red blood cells before filtration}} \times 100$$

EXAMPLE 1

An apparatus 40 for the separation of blood components configured as illustrated in FIG. 1 was fabricated by filling a tubular housing 14 made of ABS resin with defatted and bleached Egyptian cotton packed (in a total amount of 26 g) in two layers, i.e. a blood inlet side fiber aggregate layer 16 of a bulk density of 0.18 g/cm³ and a blood outlet side fiber aggregate layer 18 of a bulk density of 0.22 g/cm³. A liquid containing floating red blood cells (having a hematocrit value of 50) prepared by adding about 100 ml of phsiological saline solution to 250 ml of a concentrated solution of red blood cells 5 days old from the time of collection was caused to flow down into the apparatus at a temperature of 4° to 6° C. via the blood inlet 10 to determine ratio of removal of white blood cells, ratio of removal of blood platelets, ratio of recovery of red blood cells, and time for passage of blood. The results were as shown in Table 1.

Control 1

The same test was carried out by following the procedure of Example 1, except that the housing 14 was filled with defatted and bleached Egyptian cotton packed (in a total amount of 22 g) as a fiber aggregate in a uniform bulk density of 0.22 g/cm³. The results were as shown in Table 1.

EXAMPLE 2

The same test was carried out by following the procedure of Example 1, except that whole blood 5 days old from the time of collection was used in place of the solution containing floating red blood cells. The results were as shown in Table 1.

Control 2

The same test was carried out by following the procedure of control 1, except that whole blood 5 days old from the time of collection was used in place of the solution containing floating red blood cells. The results were as shown in Table 1.

EXAMPLE 3

An apparatus 140 for the separation of blood components configured as illustrated in FIG. 2 was fabricated by filling a tubular housing 114 made of ABS resin with defatted and bleached Egyptian cotton packed (in a total amount of 26 g) in three layers, i.e. a first blood inlet side fiber aggregate layer 116a of a bulk density of 0.18 g/cm³, a second blood inlet side fiber aggregate layer 116b of a bulk density of 0.20 g.cm³, and a blood outlet side fiber aggregate layer 118 of a bulk density of 0.22 g/cm³ A liquid containing red blood cells (having a hematocrit value of 50) prepared by adding about 100 ml of physiological saline solution to 250 ml of a concentrated solution of red blood cells 5 days old from the time of collection as caused to flow down into the apparatus at a temperature of 4° to 6° C. via the blood inlet 110 for determination of the same physical constants as in Example 1. The results were as shown in Table 1.

EXAMPLE 4

The same test was performed by following the procedure of Example 3, except that whole blood 5 days old from the day of collection was used in place of the solution containing floating red blood cells. The results were as shown in Table 1.

TABLE 1

| No. | Ratio of removal of white blood cells (%) | Ratio of removal of platelets (%) | Ratio of recovery of red blood cells (%) | Time for passage (min.) |
|---|---|---|---|---|
| Example 1 | 96 | 97 | 96 | 20 |
| Example 2 | 96 | 97 | 96 | 25 |
| Example 3 | 96 | 97 | 96 | 15 |
| Example 4 | 96 | 97 | 96 | 20 |
| Control 1 | 96 | 97 | 94 | 35 |
| Control 2 | 96 | 97 | 94 | 40 |

Industrial Applicability

As described in detail above, the apparatus for separation of blood components according to this invention is configured so that fibers capable of sequestering white blood cells and blood platelets are packed in two or three layers having magnitudes of bulk density increasing in the direction from the blood inlet side to the blood outlet side of the housing. In the actual separation of blood components, therefore, this apparatus removes white blood cells and blood platelets in substantially the same ratios as an apparatus having the same fibers packed in a uniform bulk density and yet manifests a conspicuous effect of notably shortening the time required for the treatment. It also has an advantage that the ratio of recovery of red blood cells is improved.

I claim:

1. An apparatus for separating white blood cells and blood platelets from blood, comprising:

a tubular housing having at one end thereof a blood inlet and at another end thereof a blood outlet;

a plurality of layers of staple fibers of bleached Egyptian cotton capable of sequestering white blood cells and blood platelets packed in said housing in the direction of flow of blood through said housing between said blood inlet and outlet;

said layers of fibers comprising a blood inlet side fiber layer adjacent said blood inlet and a blood outlet side fiber layer adjacent said blood outlet, said blood inlet side fiber layer having a bulk density of not less than 0.16 g/cm$^3$ and not more than 0.21 g/cm$^3$, and said blood outlet side fiber layer having a bulk density of not less than 0.21 g/cm$^3$ and not more than 0.23 g/cm$^3$;

said plurality of layers of fibers being packed in a ratio in the range of 0.04 to 0.09 g per ml of the flow volume of blood under treatment by said apparatus; and wherein the ratio by weight of said blood inlet side fiber layer to said blood outlet side fiber layer is in the range of 75:25 to 60:40, and wherein the fibers of both said blood inlet side fiber layer and blood outlet side fiber layer are substantially the same except for their respective bulk densities.

2. An apparatus according to claim 1, wherein said blood inlet side fiber layer comprises a first fiber layer of bulk density of not less than 0.16 g/cm$^3$ and not more than 0.19 g/cm$^3$ on the blood inlet side thereof, and a second fiber layer of a bulk density of not less than 0.19 g./cm$^3$ and not more than 0.21 g/cm$^3$ on the blood outlet side thereof.

3. An apparatus according to claim 2, wherein the ratio by weight of said first fiber layer to said second fiber layer of said blood inlet side fiber layer is in the range of 60:40 to 40:60.

* * * * *